US00PP29025P3

(12) United States Plant Patent
Tuszynski

(10) Patent No.: US PP29,025 P3
(45) Date of Patent: Feb. 27, 2018

(54) ***YUCCA* PLANT NAMED 'TUSZYUC001'**

(50) Latin Name: *Yucca gloriosa*
Varietal Denomination: TUSZYUC001

(71) Applicant: Grzegorz Tuszynski, Otrebusy (PL)

(72) Inventor: Grzegorz Tuszynski, Otrebusy (PL)

(73) Assignee: POULSEN ROSER A/S, Fredensborg (DK)

( * ) Notice: Subject to any disclaimer, the term of this patent is extended or adjusted under 35 U.S.C. 154(b) by 36 days.

(21) Appl. No.: 14/998,674

(22) Filed: Jan. 29, 2016

(65) Prior Publication Data

US 2017/0223885 P1 Aug. 3, 2017

(51) Int. Cl.
*A01H 5/00* (2006.01)

(52) U.S. Cl.
USPC ..... Plt./373

(58) Field of Classification Search
USPC ..... Plt./373
CPC ..... A01H 5/00; A01H 5/02; A01H 5/12
See application file for complete search history.

(56) References Cited

PUBLICATIONS

Upov Pluto Plant Variety Database 20170426 retrieved on Apr. 26, 2017, retrieved from the Internet at <http://www.upov.int/pluto/en/index.jsp> one page.*

* cited by examiner

*Primary Examiner* — June Hwu

(57) ABSTRACT

A new *yucca* plant which has attractive foliage. This new and distinct variety has shown to be uniform and stable in the resulting generations from asexual propagation.

2 Drawing Sheets

Botanical designation: *Yucca gloriosa.*
Variety denomination: 'TUSZYUC001'.

SUMMARY OF THE INVENTION

The present invention constitutes a new and distinct variety of *yucca* plant which was discovered in a cultivated, protected greenhouse area in Warsaw, Poland. The new *yucca* variety resulted from a naturally occurring mutation of unknown causation on a branch of *Yucca gloriosa* 'Variegata', a non-patented variety. The resulting mutation was selected and evaluations were conducted on the resulting *yucca* plants in a controlled environment.

The *yucca* plant of the present discovery has a unique combination of characteristics which are outstanding in the new variety and which distinguish it from the original *yucca Yucca gloriosa* 'Variegata' as well as all other varieties which we are aware of. For example, 'TUSZYUC001' has marginal intonations on the leaves the color of Red-Purple Group 58B. The original *Yucca gloriosa* Variegata has marginal leaf coloration of primarily Yellow Group 4D. Additionally the new variety is more compact than the original variety.

The criteria used to evaluate the claimed plant were selected in order to introduce a distinct variety for garden and container use with unique qualities, such as:

1. Uniform and abundant foliage with unique purple brown coloration;
2. Vigorous, but compact growth when propagated in-vitro;
3. Exceptional disease resistance.

This combination of qualities is not present in previously available commercial cultivars of this type, known to the inventor, and distinguish 'TUSZYUC001' from all other varieties of which we are aware.

Asexual reproduction of 'TUSZYUC001' by basal shoot cuttings in vitro was first done by Grzegorz Tuszynski in Warsaw, Poland in July of 2011. Plants were deflasked and rooted in ordinary peat-based growing medium. This initial and other subsequent propagations have demonstrated that the characteristics of 'TUSZYUC001' are stable and reproduced true to type in successive generations of asexual reproduction.

DESCRIPTION OF THE DRAWING

The accompanying color illustrations show as true as is reasonably possible to obtain in color photographs of this type, the typical characteristics of 'TUSZYUC001'.

Specifically illustrated in FIG. 1 of the drawings are *yucca* plants in containers, showing overall appearance and colors of leaf variegation.

Figure 1:
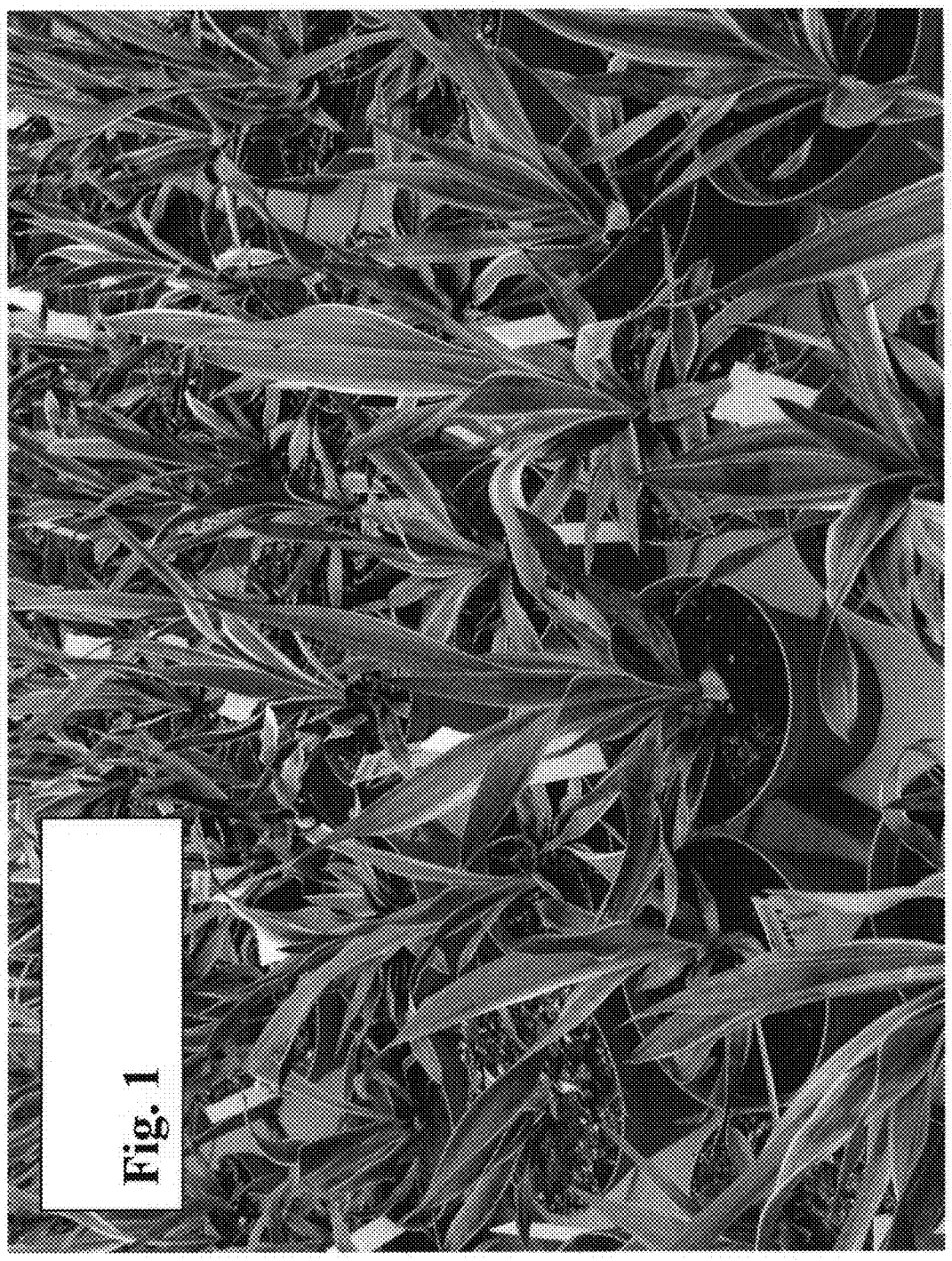
Figure 2:
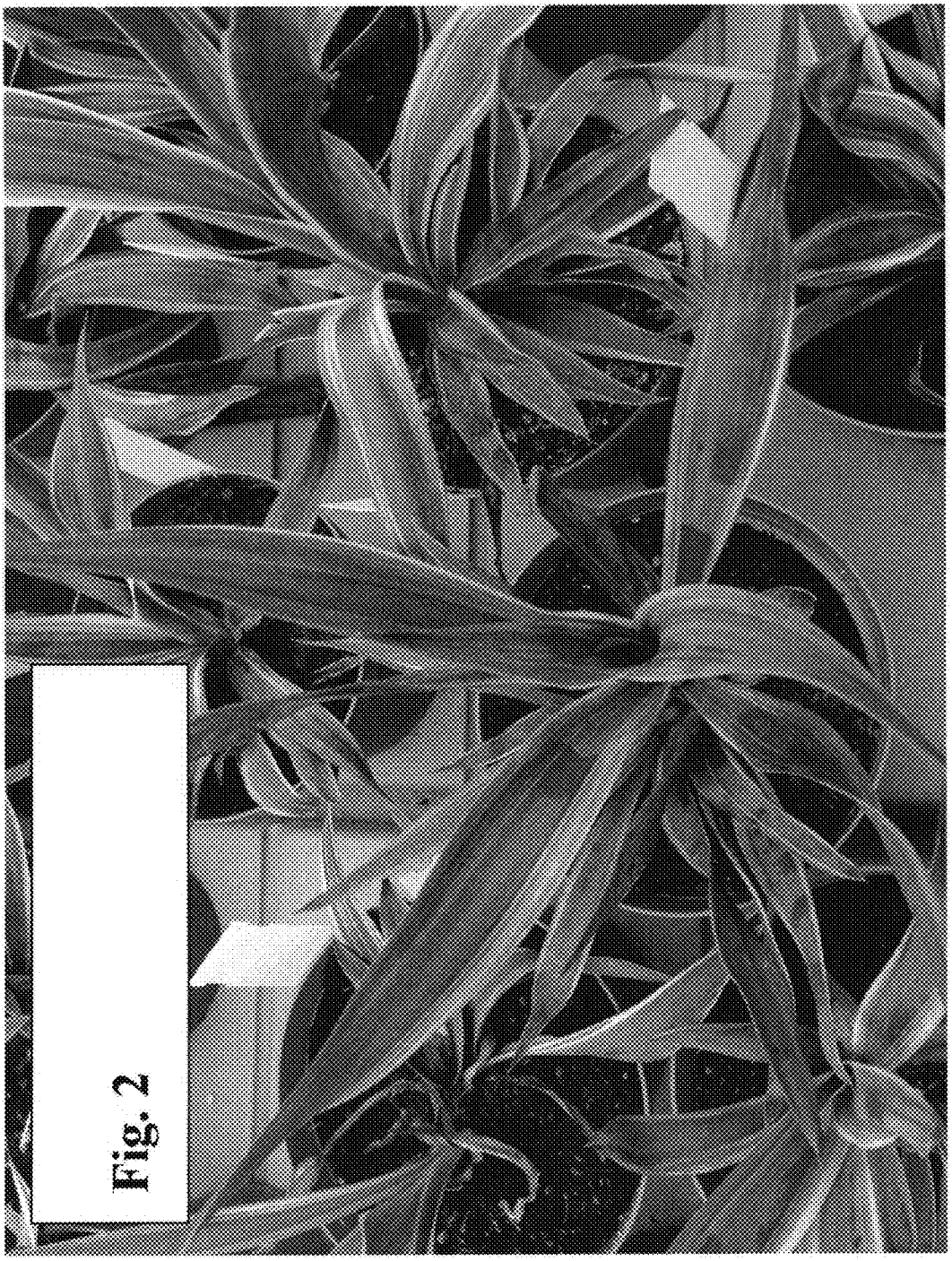

Specifically illustrated in FIG. 2 of the drawings are mature and juvenile leaves. Plants shown are approximately 2 years of age and were cultivated in a glasshouse in Warsaw, Poland.

DETAILED DESCRIPTION OF THE VARIETY

The following is a description of 'TUSZYUC001',as observed in its growth in in a glass house in Warsaw, Poland. Observed plants are 2 years of age and grown in 24 cm containers. Color references are made using The Royal Horticultural Society (London, England) Colour Chart, 2001, except where common terms of color are used.

For a comparison, physical characteristics of similar *yucca* variety 'WALBRISTAR' described in U.S. Plant Pat. No. 17,653 are compared to 'TUSZYUC001' in Chart 1.

CHART 1

| | 'TUSZYUC001' | 'WALBRISTAR' |
|---|---|---|
| Secondary color of leaf blade margins upper surface | Red-Purple Group 58B | Yellow 13A |
| Plant height | 35 cm | 50 cm |

Plant description:

*Blooming habit*.—Not observed to date. No flowers have been produced. No fruit or seed have been produced to date.

*Plant habit*.—Upright, semi-erect.

*Plant height*.—About 35 cm.

*Plant width*.—About 35 cm.

Foliage:

*Foliage type*.—Evergreen.

*Quantity of leaves*.—25 to 40.

*General leaf shape*.—Lanceolate with broadest section toward the top.

*Leaf shape cross section*.—Distally concave.

*Leaf blade attitude*.—Semi-erect.

*Leaf apex*.—Acute.

*Leaf base*.—Truncate.

*Leaf arrangement*.—Spiral.

*Shape of apical spine*.—Triangular.

*Variegation pattern*.—Parallel.

*Leaf margins*.—Entire.

*Leaf surface texture*.—Smooth.

*Leaf width*.—About 5 cm.

*Leaf length*.—About 30 cm.

*Mature leaf coloration*.—Upper: Green Group 137B and Yellow-Green Group N144A. Marginal intonations of Red-Purple Group 58B and Yellow Group 2D. Lower: Yellow-Green Group N144A with marginal intonations of Red-Purple Group 58B and Yellow Group 2D.

*Juvenile leaf coloration*.—Upper: Green Group 137B and Yellow-Green Group N144A. Marginal intonations of Greyed-Purple Group 183D, Red-Purple Group 58B and Yellow Group 2D. Lower: Yellow-Green Group N144A with marginal intonations of Greyed-Purple Group 183D and Yellow Group 2D. Leaf coloration remains the same throughout the growing season.

*Disease resistance*.—Average resistance leaf spot *Cercospora concentrica* or *Coniothyrium concentricum*.

I claim:

1. A new and distinct variety of *yucca* plant named 'TUSZYUC001', substantially as illustrated and described herein.

* * * * *